US008682449B2

(12) United States Patent
Simon (10) Patent No.: US 8,682,449 B2
(45) Date of Patent: Mar. 25, 2014

(54) METHODS AND APPARATUS FOR TRANSCRANIAL STIMULATION

(75) Inventor: Bruce J. Simon, Mountain Lakes, NJ (US)

(73) Assignee: Electrocore, LLC, Basking Ridge, NJ (US)

(*) Notice: Subject to any disclaimer, the term of this patent is extended or adjusted under 35 U.S.C. 154(b) by 1244 days.

(21) Appl. No.: 12/548,569

(22) Filed: Aug. 27, 2009

(65) Prior Publication Data

US 2009/0319002 A1    Dec. 24, 2009

Related U.S. Application Data

(63) Continuation-in-part of application No. 12/394,972, filed on Feb. 27, 2009, now Pat. No. 8,401,650, which is a continuation-in-part of application No. 12/338,191, filed on Dec. 18, 2008, now Pat. No. 8,209,034.

(60) Provisional application No. 61/043,802, filed on Apr. 10, 2008, provisional application No. 61/043,805, filed on Apr. 10, 2008.

(51) Int. Cl.
*A61N 1/36* (2006.01)

(52) U.S. Cl.
USPC .............................. 607/115; 607/45; 607/139

(58) Field of Classification Search
USPC ........................................... 607/45, 115, 139
See application file for complete search history.

(56) References Cited

U.S. PATENT DOCUMENTS

| 4,198,936 | A | 4/1980 | Pagel et al. |
| 4,304,239 | A | 12/1981 | Perlin |
| 4,351,330 | A | 9/1982 | Scarberry |
| 4,574,807 | A | 3/1986 | Hewson et al. |
| 4,640,298 | A | 2/1987 | Pless et al. |
| 4,706,688 | A | 11/1987 | Don Michael et al. |
| 4,817,611 | A | 4/1989 | Arzbaecher et al. |
| 4,919,147 | A | 4/1990 | Reinhardt et al. |
| 5,003,991 | A | 4/1991 | Takayama et al. |

(Continued)

FOREIGN PATENT DOCUMENTS

| WO | WO 01/00273 | 1/2001 |
| WO | WO 2005/007120 | 1/2005 |
| WO | WO 2009/137683 | * 11/2009 |

OTHER PUBLICATIONS

International Search Report and Written Opinion for Corresponding PCT Application PCT/US09/36259, May 11, 2009.

*Primary Examiner* — Carl H Layno
*Assistant Examiner* — Jennifer Ghand
(74) *Attorney, Agent, or Firm* — Dentons US LLP (57) ABSTRACT

Systems, apparatus and methods are described for applying electric current to neurons in the brain to treat disorders and to improve motor and/or memory functions in a patient. In a method according to the invention, an electrode is positioned adjacent to and spaced from the skin surface of the patient's head and an electric current is applied through the electrode to a target region in the brain to modulate one or more neurons in the target region. The electrode is housed within an enclosure and spaced from the skin surface so that the electrode does not directly contact the patient's tissue, which reduces the potential for collateral tissue damage or necrosis and shields the electrode from the patient's tissue which substantially inhibits Faradic products (e.g., $H^+$, $OH^-$, $H_2O_2$) of the electrode from reaching the target site.

20 Claims, 4 Drawing Sheets

(56) References Cited

U.S. PATENT DOCUMENTS

| | | |
|---|---|---|
| 5,056,532 A | 10/1991 | Hull et al. |
| 5,249,585 A | 10/1993 | Turner et al. |
| 5,366,490 A | 11/1994 | Edwards et al. |
| 5,370,675 A | 12/1994 | Edwards et al. |
| 5,370,679 A | 12/1994 | Atlee, III |
| 5,431,696 A | 7/1995 | Atlee, III |
| 5,540,730 A | 7/1996 | Terry, Jr. et al. |
| 5,626,618 A | 5/1997 | Ward et al. |
| 5,692,506 A | 12/1997 | Linder |
| 5,707,400 A | 1/1998 | Terry, Jr. et al. |
| 5,800,378 A | 9/1998 | Edwards et al. |
| 5,967,977 A | 10/1999 | Mullis et al. |
| 6,006,138 A | 12/1999 | Don Michael |
| 6,083,249 A | 7/2000 | Familoni |
| 6,083,255 A | 7/2000 | Laufer et al. |
| 6,148,222 A | 11/2000 | Ramsey, III |
| 6,198,970 B1 | 3/2001 | Freed et al. |
| 6,327,503 B1 | 12/2001 | Familoni |
| 6,341,236 B1 | 1/2002 | Osorio et al. |
| 6,347,247 B1 | 2/2002 | Dev et al. |
| 6,356,786 B1 | 3/2002 | Rezai et al. |
| 6,356,787 B1 | 3/2002 | Rezai et al. |
| 6,366,814 B1 | 4/2002 | Boveja et al. |
| 6,423,058 B1 | 7/2002 | Edwards et al. |
| 6,425,877 B1 | 7/2002 | Edwards |
| 6,438,423 B1 | 8/2002 | Rezai et al. |
| 6,609,030 B1 | 8/2003 | Rezai et al. |
| 6,610,713 B2 | 8/2003 | Tracey |
| 6,656,960 B2 | 12/2003 | Puskas |
| 6,778,854 B2 | 8/2004 | Puskas |
| 6,819,956 B2 | 11/2004 | DiLorenzo |
| 6,865,416 B2 | 3/2005 | Dev et al. |
| 6,871,092 B2 | 3/2005 | Piccone |
| 6,885,888 B2 | 4/2005 | Rezai |
| 6,934,583 B2 | 8/2005 | Weinberg et al. |
| 6,937,896 B1 | 8/2005 | Kroll |
| 6,955,173 B2 | 10/2005 | Lesh |
| 6,980,865 B1 | 12/2005 | Wang et al. |
| 7,008,419 B2 | 3/2006 | Shadduck |
| 7,043,307 B1 | 5/2006 | Zelickson et al. |
| 7,072,720 B2 | 7/2006 | Puskas |
| 7,081,115 B2 * | 7/2006 | Taimisto ............... 606/41 |
| 7,142,910 B2 | 11/2006 | Puskas |
| 7,167,750 B2 | 1/2007 | Knudson et al. |
| 7,229,469 B1 | 6/2007 | Witzel et al. |
| 7,292,890 B2 | 11/2007 | Whitehurst et al. |
| 7,310,552 B2 | 12/2007 | Puskas |
| 7,326,207 B2 | 2/2008 | Edwards |
| 7,400,929 B2 | 7/2008 | Zelickson et al. |
| 8,239,030 B1 * | 8/2012 | Hagedorn et al. ............... 607/45 |
| 2001/0031941 A1 | 10/2001 | Edwards et al. |
| 2002/0010495 A1 | 1/2002 | Freed et al. |
| 2002/0016344 A1 | 2/2002 | Tracey |
| 2002/0016615 A1 | 2/2002 | Dev |
| 2002/0116030 A1 | 8/2002 | Rezai |
| 2002/0183682 A1 | 12/2002 | Darvish et al. |
| 2002/0198570 A1 | 12/2002 | Puskas |
| 2003/0009208 A1 | 1/2003 | Snyder et al. |
| 2003/0074039 A1 | 4/2003 | Puskas |
| 2003/0195593 A1 | 10/2003 | Ingle et al. |
| 2004/0039431 A1 | 2/2004 | Machold et al. |
| 2004/0059383 A1 | 3/2004 | Puskas |
| 2004/0172075 A1 | 9/2004 | Shafer et al. |
| 2004/0249416 A1 | 12/2004 | Yun et al. |
| 2005/0021092 A1 | 1/2005 | Yun et al. |
| 2005/0065553 A1 | 3/2005 | Ben Ezra et al. |
| 2005/0065562 A1 | 3/2005 | Rezai |
| 2005/0065573 A1 | 3/2005 | Rezai |
| 2005/0075701 A1 | 4/2005 | Shafer |
| 2005/0075702 A1 | 4/2005 | Shafer |
| 2005/0125044 A1 | 6/2005 | Tracey |
| 2005/0143412 A1 | 6/2005 | Puskas |
| 2005/0149146 A1 | 7/2005 | Boveja et al. |
| 2005/0153885 A1 | 7/2005 | Yun |
| 2005/0165388 A1 | 7/2005 | Bhola |
| 2005/0182463 A1 | 8/2005 | Hunter et al. |
| 2005/0216062 A1 | 9/2005 | Herbst |
| 2005/0240241 A1 | 10/2005 | Yun |
| 2005/0256028 A1 | 11/2005 | Yun |
| 2005/0273146 A1 | 12/2005 | DeSimone et al. |
| 2006/0129215 A1 | 6/2006 | Helmus et al. |
| 2006/0135998 A1 | 6/2006 | Libbus et al. |
| 2006/0167498 A1 | 7/2006 | DiLorenzo |
| 2006/0259107 A1 | 11/2006 | Caparso et al. |
| 2007/0106337 A1 | 5/2007 | Errico et al. |
| 2007/0106338 A1 | 5/2007 | Errico |
| 2007/0106339 A1 | 5/2007 | Errico et al. |
| 2007/0179558 A1 * | 8/2007 | Gliner et al. ............... 607/45 |
| 2007/0191902 A1 | 8/2007 | Errico et al. |
| 2007/0213645 A1 | 9/2007 | Zumeris et al. |
| 2007/0225768 A1 | 9/2007 | Dubak |
| 2008/0039904 A1 | 2/2008 | Bulkes et al. |
| 2011/0190846 A1 * | 8/2011 | Ruffini et al. ............... 607/45 |
| 2011/0288610 A1 * | 11/2011 | Brocke ............... 607/45 |
| 2012/0209346 A1 * | 8/2012 | Bikson et al. ............... 607/45 |

* cited by examiner

METHODS AND APPARATUS FOR TRANSCRANIAL STIMULATION

CROSS REFERENCE TO RELATED APPLICATIONS

The present application is a continuation-in-part of U.S. patent application Ser. No. 12/394,972, now U.S. Pat. No. 8,401,650, filed Feb. 27, 2009, which claims the benefit of provisional patent application Ser. Nos. 61/043,805 and 61/043,802, filed Apr. 10, 2007, and which is a continuation-in-part of U.S. patent application Ser. No. 12/338,191, now U.S. Pat. No. 8,209,034, filed Dec. 18, 2008 the complete disclosures of which are incorporated herein by reference for all purposes. This application is also related to commonly assigned co-pending U.S. patent Ser. Nos. 11/555,142, 11/555,170, 11/592,095, now U.S. Pat. No. 7,725,188, Ser. No. 11/591,340, now U.S. Pat. No. 7,747,324, Ser. No. 11/591,768, now U.S. Pat. No. 7,711,430, Ser. Nos. 11/754, 522, 11/735,709, and 12/246,605 the complete disclosures of which are incorporated herein by reference for all purposes.

BACKGROUND OF THE INVENTION

The present invention relates to the delivery of electrical energy to bodily tissues for therapeutic purposes, and more specifically to devices and methods for treating various disorders resulting from nerve transmissions in the brain.

The use of electrical stimulation for treatment of medical conditions has been well known in the art for nearly two thousand years. Electrical stimulation of the brain and the peripheral nervous system and/or direct stimulation of malfunctioning tissue are generally a completely reversible and non-destructive treatment and holds significant promise for the treatment of many ailments.

Transcranial direct current stimulation (tDCS) is being studied for treatment of a number of conditions, such as improving motor performance in healthy people, improving memory consolidation, accelerating recovery from major stroke and the treatment of migraines, bipolar disease, epilepsy, schizophrenia and major depression. tDCS typically involves the application of low frequency oscillatory currents or weak direct currents (e.g., about 1-2 mA) to modulate the activity of targeted neurons in the brain. Typically, the electrode associated with the positive pole or anode causes an increase in nerve activity while the electrode associated with the negative pole or cathode causes a decrease in nerve activity.

Several generations of neurophysiologic experiments have shown that neurons respond to static (DC) electrical fields by altering their firing rates. Firing increases when the anode is located near the cell body and decreases when the field is reversed. However, when the electrodes are placed on the scalp, the current density produced in the brain is exceedingly small, changing membrane potentials only by a fraction of a millivolt. tDCS typically only influences the area of the brain directly underneath the electrode that is close to the skull and thus is more selective than other methods of brain stimulation. Transcranial direct current stimulation is not "stimulation" in the same sense as transcranial magnetic stimulation or the stimulation of the brain and nerves with conventional techniques. It does not appear to cause nerve cell firing on its own and does not produce discrete effects such as the muscle twitches associated with classical stimulation.

Schizophrenics often have what are called negative symptoms. Negative symptoms include apathy, poor attention, poor grooming habits and poor motivation. These symptoms have been associated with under activity of the frontal lobes, particularly a brain area called the left dorsolateral prefrontal cortex (LDPFC). Positive schizophrenic symptoms such as hallucinations may be associated with over activity in different brain areas, like the temporal cortex. Thus, tDCS may be able to up regulate activity in the left dorsolateral prefrontal cortex while simultaneously decreasing activity in the temporal cortex. This could have a substantial impact on a range of schizophrenic symptoms. For depression, tDCS may be able to up regulate activity in the left dorsolateral prefrontal cortex while simultaneously decreasing activity in the right dorsolateral prefrontal cortex. This will likely have a more robust antidepressant effect.

One of the limitations of current tDCS is that the electric current can only be applied for a limited period of time and at a limited power or voltage because the electrodes will begin to damage the tissue they are in contact with. In light of this, improved systems, devices and methods for the treatment of disorders associated with nerve transmissions in the brain are desired.

SUMMARY OF THE INVENTION

The present invention provides systems, apparatus and methods for selectively applying electrical energy to body tissue. Specifically, the present invention includes systems and methods for applying low frequency oscillatory and/or direct current to neurons in the brain to treat disorders or to improve motor and/or memory functions in a patient.

In one aspect of the invention, an electrode is positioned adjacent to and spaced from the skin surface of the patient's head and a low frequency oscillatory or direct current is applied through the electrode to a target region in the brain to modulate, stimulate and/or inhibit one or more neurons in the target region. In a preferred embodiment, the electrode is housed within an enclosure and a portion of the enclosure is positioned in contact with the skin surface. Thus, the electrode does not directly contact the patient's tissue, which reduces the potential for collateral tissue damage or necrosis and/or excessive electric fields in the tissue. The enclosure physically shields the electrode from the patient's tissue which substantially inhibits Faradic products (e.g., $H^+$, $OH^-$, $H_2O_2$) of the electrode from reaching the target site. In this manner, an electric current can be applied to the electrode(s) without the danger of such Faradic products reaching excessively high concentrations at the tissue site. In addition, electric current can be delivered for a longer period of time and/or at higher power levels than is conventionally considered safe.

In certain embodiments, the electrode is the positive pole or anode which causes an increase in firing of neurons located close to the electrode. This up regulates these neurons and increases their overall activity. In other embodiments, the electrode is the negative pole or cathode which causes a decrease in firing of neurons or down regulation of these neurons. In yet other embodiments, the invention includes both an anode and a cathode to increase the activity of certain neurons while simultaneously decreasing the activity of other neurons within the brain.

In a preferred embodiment, one or more enclosure(s) are positioned against the patient's head and conductive fluid is delivered within the interior of each enclosure. Electrical energy is applied to the conductive fluid such that the electrical energy passes through an ion-permeable section of one portion of the enclosure to the target region within the brain. In an exemplary embodiment, the electrical energy is applied to an electrode positioned within a fluid passage or tube coupled to an electrically conductive contact element, such as a conducting gel-like material (e.g., hydrogel or the like). The contact element is designed to conform to the patient's head and provide good electrical contact to the skin surface. The fluid passage extends away from the contact element to space the electrode from the patient's tissue. The electrode may be spaced from about 1-20 cm, preferably between about 3-8 cm, from the contact element.

In certain embodiments, the treatment electrode and the enclosure are placed adjacent to or near the motor cortex of the brain. In these embodiments, an electrical signal is applied to neurons within the motor cortex to improve motor performance in healthy people and/or to accelerate recovery from motor function loss (e.g., major stroke).

In other embodiments, the treatment electrode and the enclosure are placed adjacent to or near a target region in the brain that is underactive or overactive, thereby resulting in a disorder such as acute pain, epilepsy, fibromyalgia, schizophrenia and major depression. In one such embodiment, an anode electrode is placed near the left dorsolateral prefrontal cortex (LDPFC) to increase the activity of the neurons in this region to treat schizophrenia. In this embodiment, a cathode electrode may also be placed adjacent to or near the temporal cortex to decrease activity in this area. In the exemplary embodiment, the electrodes will up regulate activity in the LDPFC while simultaneously down regulating activity in the temporal cortex to treat a range of schizophrenia symptoms.

In yet another embodiment, an anode electrode is placed adjacent to or near the left dorsolateral prefrontal cortex and a cathode electrode is placed adjacent to or near the right dorsolateral prefrontal cortex. This will increase activity in the LDPFC while decreasing activity in the RDPFC to treat major depression.

In one embodiment, the device further includes a vacuum source for aspirating the electrically conductive fluid from the interior of the enclosure(s). The vacuum source may be a positive source of aspiration with an aspiration passage coupled to the interior of each enclosure or the device may be designed to simply allow the fluid to evacuate the enclosure(s) through the same fluid passage it entered through pressure differential, gravity, or the like. Evacuating the conductive fluid deflates the enclosure(s) and allows any excess Faradic products and/or heat to be evacuated from the device. In this manner, the enclosure(s) may be periodically evacuated to allow for periodic evacuation of excess Faradic products and heat, which allows for higher power levels and/or longer continuous use of the device in the patient. In some embodiments, the device may be adapted for continuous circulation of the electrically conductive fluid to reduce any build-up of heat or Faradic products and ensure uniform temperatures at the outer surface of the enclosure(s). These embodiments will allow the device to use much higher power levels as the heat generated around the electrode(s) and within the conductive fluid from the higher power levels will be continuously evacuated from the interior of the enclosure(s).

The source of electrical energy is preferably an electrical signal generator that operates to generate either a low frequency oscillatory current (e.g., less than 100 Hz, preferably between about 0 to 60 Hz) or a direct current of between about 0.01 to 100 mA, more preferably between about 1-10 mA inclusive.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise arrangements and instrumentalities shown.

DETAILED DESCRIPTION OF THE PREFERRED EMBODIMENTS

In the present invention, electrical energy is applied to one or more electrodes in the presence of an electrically conductive fluid to deliver an electrical signal to a patient. For convenience, the remaining disclosure will be directed specifically to the application of a low frequency oscillatory and/or weak direct current to one or more target regions within a patient's brain to treat the symptoms of certain disorders, such as epilepsy, depression, Parkinson's disease, stroke and schizophrenia and/or improve motor functions, improve working or declaratory memory and/or memory consolidation. Suitable methods for performing such transcranial current stimulation are described in W. Paulus, "Transcranial Magnetic Stimulation and Transcranial Direct Current Stimulation" (Supplements to Clinical Neurophysiology, volume 56) and US Patent Application Publication No. 20080208287 to Palermo, the complete disclosures of which are incorporated herein by reference. However, it will be appreciated that the systems and methods of the present invention can be applied equally well to other tissues and nerves of the body, including but not limited to cranial nerves, such as parasympathetic nerves, sympathetic nerves, spinal nerves, facial nerves, vestibulocochlear nerves, enteric nerves and the like.

Figure 1:
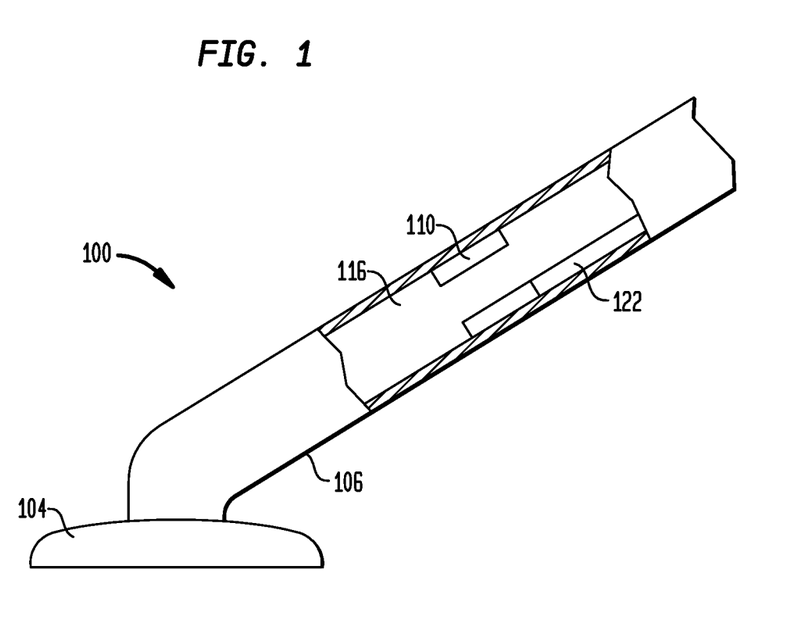
FIG. 1 is a cross-sectional view of an electrode device in accordance with one or more aspects of the present invention.

With reference to FIG. 1, an exemplary device 100 for delivering an electrical signal to a patient will now be described. Device 100 is designed to be positioned in contact with an outer skin surface of a patient at a location that (when activated) achieves a therapeutic result. The device 100 includes an enclosure for shielding the electrode(s) from direct contact with the patient's skin. In the exemplary embodiment, the enclosure includes a contact element 104 fluidly coupled to a fluid tube 106. An electrode 110 is located within the interior of fluid tube 106. In certain embodiments, electrode 110 will comprise a positive pole or anode that typically causes an increase in firing of neurons located close to the electrode 110. This up regulates these neurons and increases their overall activity. In other embodiments, electrode 110 will comprise a negative pole or cathode that typically causes a decrease in firing of neurons or down regulation of these neurons.

For convenience, only one device 100 has been illustrated. However, it will be understood by those skilled in the art that multiple devices 100 may be employed. For example, in certain embodiments, the invention will utilize two devices 100 each having an electrode 110 of opposite polarity (i.e., an anode and a cathode) such that the electric current will pass from one of the electrodes through the patient to the other electrode. In exemplary embodiments, the invention includes both an anode and a cathode to increase the activity of certain neurons while simultaneously decreasing the activity of other neurons within the brain.

In other embodiments, one of the electrodes (either the cathode or the anode) may act as a non-treatment electrode if up regulation and/or down regulation of only one area of the brain is desired. This can be accomplished by a variety of means known in the art (i.e., electrodes with large surface areas act as suitable non-treatment or return electrodes as they tend to have low current densities). In such embodiments, the non-treatment or return electrode may be positioned such that the electric current flows from treatment electrode 110 through a specific target location in the patient's brain (near treatment electrode 110) directly to the non-treatment electrode. In other embodiments, the non-treatment or return electrode may be positioned such that when applied to the patient, the current passes out from electrode 110 in a substantially radial pattern—in other words, the pattern of the electro-magnetic field emanating from the electrode 110 is not focused on any particular point, or small, localized region of the patient's anatomy. This is preferably achieved by applying the return electrode to an external portion of the patient, such as to at least one of the upper-back, the chest, and/or the stomach The contact element 104 preferably comprises an electrically conductive material that will conform to the patient's head. By way of example, contact element 104 may be substantially formed from a biocompatible electrically conductive gel-like material, such as a hydrogel. However, it will be recognized by those skilled in the art that a variety of commercially available materials may be used to carry out the present invention.

As shown in FIG. 1, fluid tube 106 includes an internal lumen 116 coupled to a source of electrically conductive fluid (not shown) and to contact element 104. At least one electrode 110 is positioned within lumen 116 and coupled thereto (such as by a UV curable adhesive, such as Dymax 204-CTH). Fluid tube 106 may be of a standard type formed out of polyurethane with a length sufficient to couple contact element 104 to the fluid source, and having an inside diameter of about 5 mm (although other lengths, diameters, and materials may be employed). Electrode 110 is preferably coupled to internal lumen 116 about 1-20 cm away from contact element 104, preferably about 3-8 cm. Spacing electrode 110 a suitable distance from contact element 104 ensures that Faradic products from electrode 110 do not pass through contact element 104 to the patient's tissue. The greater the distance between contact element 104 and electrode 110, the longer it will take for these Faradic products to move along lumen 116 to contact element 104.

Electrode 110 may be of a general annular or cylindrical shape and may extend around the internal surface of passage 116. Although there are a number of sizes and shapes that would suffice to implement the electrode 110, by way of example, the at least one electrode 110 may be between about 1.0-1.5 mm long (such as 1.27 mm) and may have an inside diameter of between about 2.5-2.75 mm (such as 2.67 mm). A suitable electrode 110 may be formed from Ag/AgCl or Pt—IR (90%/10%), although other materials or combinations or materials may be used, such as platinum, tungsten, gold, copper, palladium, silver or the like.

Those skilled in the art will also recognize that a variety of different shapes and sizes of electrodes may be used. By way of example only, electrode shapes according to the present invention can include ball shapes, twizzle shapes, spring shapes, twisted metal shapes, annular, solid tube shapes or the like. Alternatively, the electrode(s) may comprise a plurality of filaments, rigid or flexible brush electrode(s), coiled electrode(s) or the like. Alternatively, the electrode may be formed by the use of formed wire (e.g., by drawing round wire through a shaping die) to form electrodes with a variety of cross-sectional shapes, such as square, rectangular, L or V shaped, or the like.

A conductor 122 extends through the lumen 116 of tube 106 and electrically connects to the electrode 110. By way of example, the conductor 122 may be a solid silver wire of about 0.25 mm diameter insulated with a PTFE material of about 0.33 mm diameter. The diameter of the insulating material of the conductor 122 should be less than the internal diameter of tube 106 such that fluid may freely flow therein despite the presence of the conductor 122. The conductor 122 may be laser welded to the electrode 110 using known procedures.

A fluid, preferably a saline solution, passes into the tube 106 to substantially fill lumen 116 and provide a conductive pathway from electrode 110 to contact element 104. This configuration has several advantages over conventional electrode configurations, such as: (i) the metal of the electrode 110 is not too close to, and never comes in contact with, the patient's tissue, which means that there is no concern about tissue necrosis or excessive electric fields in the tissue; (ii) the electrode 110 may be used with direct current signal sources since any Faradic Products (e.g. $H^+$, $OH^-$, $H_2O_2$) would not reach excessively high concentrations at the tissue site; and (iii) the material of the contact element 104 is preferably very soft and flexible such that it gently conforms to the surrounding tissue.

The electrical properties of the electrode 110, the conductive fluid, and the material of the contact element 104 are preferably designed such that a resistance therethrough is no more than about 1000 Ohms, preferably no more than 500 Ohms and more preferably 200 Ohms or less. In an exemplary embodiment, the impedance through the electrode 110, the fluid, and the material of the contact element 104 should be no more than about 200 Ohms at 1000 Hz. The electrical properties of the fluid may be as important as those of the electrode 110 in this regard. The electrically conducting fluid should have a threshold conductivity to provide a suitable conductive path between electrode 110 and contact element 104. The electrical conductivity of the fluid (in units of milliSiemans per centimeter or mS/cm) will typically be between about 1 mS/cm and 200 mS/cm and will usually be greater than 10 mS/cm, preferably will be greater than 20 mS/cm and more preferably greater than 50 mS/cm. In one embodiment, the electrically conductive fluid is isotonic saline, which has a conductivity of about 17 mS/cm. Applicant has found that a more conductive fluid, or one with a higher ionic concentration, will usually provide optimal results. For example, a saline solution with higher levels of sodium chloride than conventional saline (which is on the order of about 0.9% sodium chloride) e.g., on the order of greater than 1% or between about 3% and 20%, may be desirable. A fluid of about 5% saline (e.g., approximately 100 mS/cm) is believed to work well, although modifications to the concentration and the chemical make-up of the fluid may be determined through simple experimentation by skilled artisans. In certain embodiments, for example, a buffered conductive solution may be used to further mitigate contact between Faradic Products and the patient's skin.

In an alternative embodiment, the electrode 110 may be implemented via the fluid itself. Although a 5% saline solution would have a relatively high resistance compared to a metal electrode 110 implementation, those skilled in the art would appreciate that higher conductivity fluid solutions may be employed for such purposes or a larger diameter and/or shorter tube may be utilized to increase the conductivity. Additionally or alternatively, the conductor 122 may be implemented using the conductive fluid; indeed, such fluid is within the lumen 116 anyway. Again, relatively high conductivity fluid would be desirable.

Figure 2:
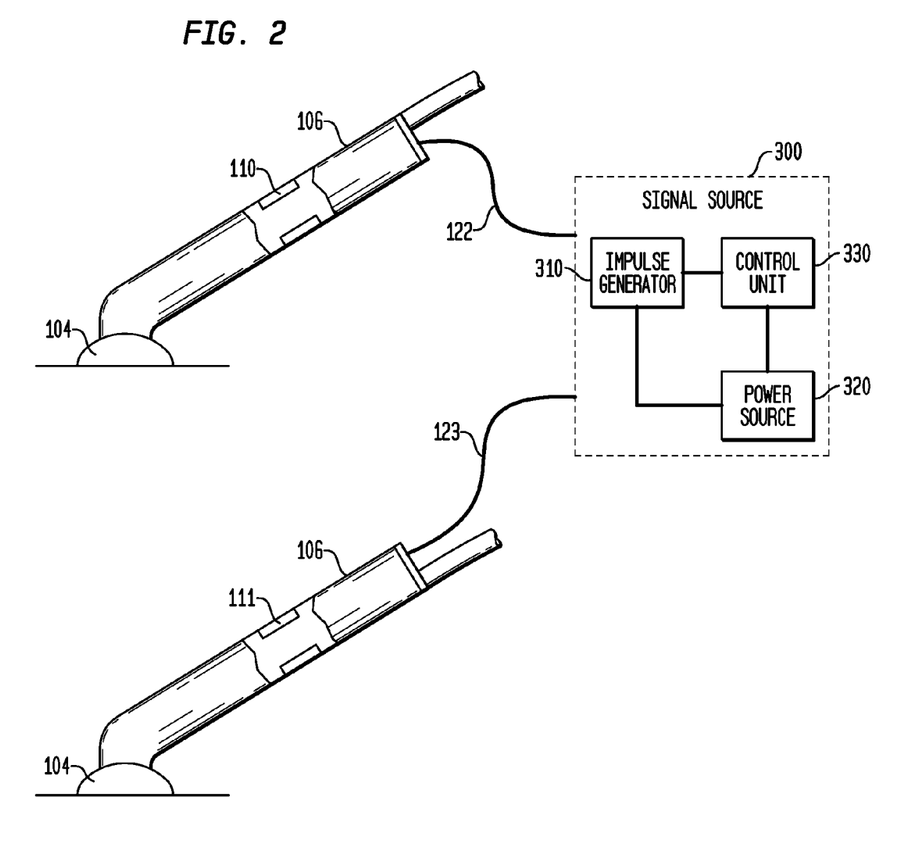
FIG. 2 is a schematic diagram of an electrical signal generating system for use with the electrode device of FIG. 1.

With reference to FIG. 2, a complete system for using the device 100 includes an electrical source 300, such as an impulse generator. In this embodiment, source 300 is configured to apply either a low frequency oscillatory current or a relatively weak direct current to device 100. Source 300 operates to apply at least one electrical signal to the conductors 122, 123 such that, when the contact element 104 is positioned at the target region on the patient, an electrical impulse passes through the electrode(s) 110, 111 to the anatomy of the patient in the vicinity of the target region to achieve a therapeutic result.

In certain embodiments, electrical source is designed to apply a low frequency oscillatory current through connectors 122, 123 to electrode(s) 110, 111 (e.g., less than 100 Hz, preferably between about 0 to 60 Hz). In these embodiments, the source 300 may be tailored for the treatment of a particular ailment and may include an electrical impulse generator 310, a power source 320 coupled to the electrical impulse generator 310, and a control unit 330 in communication with the electrical impulse generator 310 and the power source 320 (see FIG. 2). Electrodes 110, 111 provide source and return paths for the at least one electrical signal to/from the electrodes 110, 111. The control unit 330 may control the electrical impulse generator 310 for generation of the signal suitable for amelioration of the ailment when the signal is applied via the electrodes 110, 111 to the device 100. For example, the signal may have a pulse duration of between about 10-1000 us and an amplitude of between about 1-20 volts.

The control unit 330 may control the electrical impulse generator 310 for generation of the signal suitable for amelioration of the ailment when the signal is applied via the connectors 122, 123 to the electrodes 110, 111. It is noted that source 300 may be referred to by its function as a pulse generator.

In other embodiments, electrical source 300 is a direct current source for applying a direct current through lead conductor 122 to electrode(s) 110, 111. The direct current is preferably between about 0.1 mA to about 100 mA, more preferably between about 1-10 mA inclusive.

In a preferred embodiment of the present invention, a device for mild brain stimulation is disclosed. Recent studies have indicated that motor skill learning may be enhanced by applying a mild electrical current to a motor control area of the brain (see study conducted by the National Institute of Health and presented in the Jan. 20, 2009 early online edition of the Proceedings of the National Academy of Sciences). Patients receiving this current were significantly better able to learn and perform a complex motor task than those in the control groups. The findings could hold promise for enhancing rehabilitation for people with traumatic brain injury, stroke and other conditions. Motor skills which are used for activities from typing to driving, to sports, require practice and learning over a prolonged period of time. During practice, the brain encodes information about how to perform the task, but even during periods of rest, the brain is still working to strengthen the memory of doing the task. This process is known as consolidation. During practice, one group received 20 minutes of transcranial direct current stimulation (tDCS), which involves mild electrical stimulation applied through surface electrodes on the head; and works by modulating the excitability of cells in the brain's outermost layers, such as the primary motor cortex.

Transcranial direct current stimulation is being studied for treatment of a number of conditions, such as improving motor performance in healthy people, accelerating recovery from major stroke (in combination with occupational therapy) and the treatment of acute pain, epilepsy, fibromyalgia, schizophrenia and major depression. Schizophrenics often have what are called negative symptoms. Negative symptoms include apathy, poor attention, poor grooming habits and poor motivation. These symptoms have been associated with under activity of the frontal lobes, particularly a brain area called the left dorsolateral prefrontal cortex (LDPFC). Positive schizophrenic symptoms such as hallucinations may be associated with over activity in different brain areas, like the temporal cortex. Thus, tDCS may be able to up regulate activity in the left dorsolateral prefrontal cortex while simultaneously decreasing activity in the temporal cortex. This could have a substantial impact on a range of schizophrenic symptoms. For depression, tDCS may be able to up regulate activity in the left dorsolateral prefrontal cortex while simultaneously decreasing activity in the right dorsolateral prefrontal cortex. This will likely have a more robust antidepressant effect.

Transcranial direct current stimulation typically involves the application of weak electrical currents (e.g., 0.5-10 mA, preferably about 1-2 mA) to modulate the activity of targeted neurons in the brain. Several generations of neurophysiologic experiments have shown that neurons respond to static (DC) electrical fields by altering their firing rates. Firing increases when the positive pole or electrode (anode) is located near the cell body or dendrites and decrease when the field is reversed. However, when the electrodes are placed on the scalp, the current density produced in the brain is exceedingly small, changing membrane potentials only by a fraction of a millivolt. tDCS typically only influences the area of the brain directly underneath the electrode that is close to the skull and thus is more selective than other methods of brain stimulation. Transcranial direct current stimulation is not "stimulation" in the same sense as transcranial magnetic stimulation or the stimulation of the brain and nerves with conventional techniques. It does not appear to cause nerve cell firing on its own and does not produce discrete effects such as the muscle twitches associated with classical stimulation.

Transcranial direct current stimulation has also been shown to modulate excitability in the motor, visual, and prefrontal cortex. Periods rich in slow-wave sleep (SWS) not only facilitate the consolidation of declarative memories, but in humans, SWS is also accompanied by a pronounced endogenous transcortical DC potential shift of negative polarity over frontocortical areas. To induce widespread extracellular negative DC potentials, it has been shown that application of anodal tDCS ($0.26$ mA/cm$^2$) repeatedly (over 30 min) bilaterally at frontocortical electrode sites during a retention period rich in SWS can result in increased retention of declarative memories (word pairs) and also nondeclarative memories (mirror tracing skills) learned previously. It has been speculated that the effects of tDCS involve enhanced generation of slow oscillatory EEG activity considered to facilitate processes of neuronal plasticity. Shifts in extracellular ionic concentration in frontocortical tissue (expressed as negative DC potentials during SWS) may facilitate sleep-dependent consolidation of declarative memories.

One of the limitations of current tDCS is that the direct current can only be applied for a limited period of time and at a limited power or voltage because the electrodes will begin to damage the tissue they are in contact with. The present invention solves this problem by providing an electrode device designed to space the electrode from the patient's tissue.

Figure 3A:
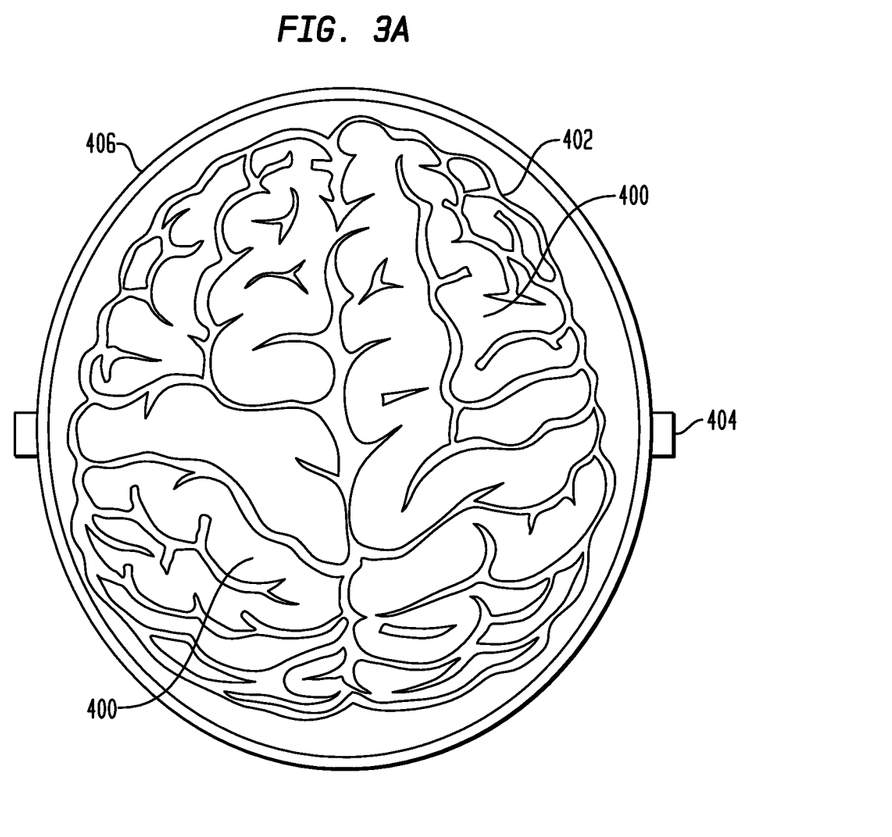
FIGS. 3A and 3B illustrate a method of treating nerve disorders in the brain according to the present invention.
Figure 3B:
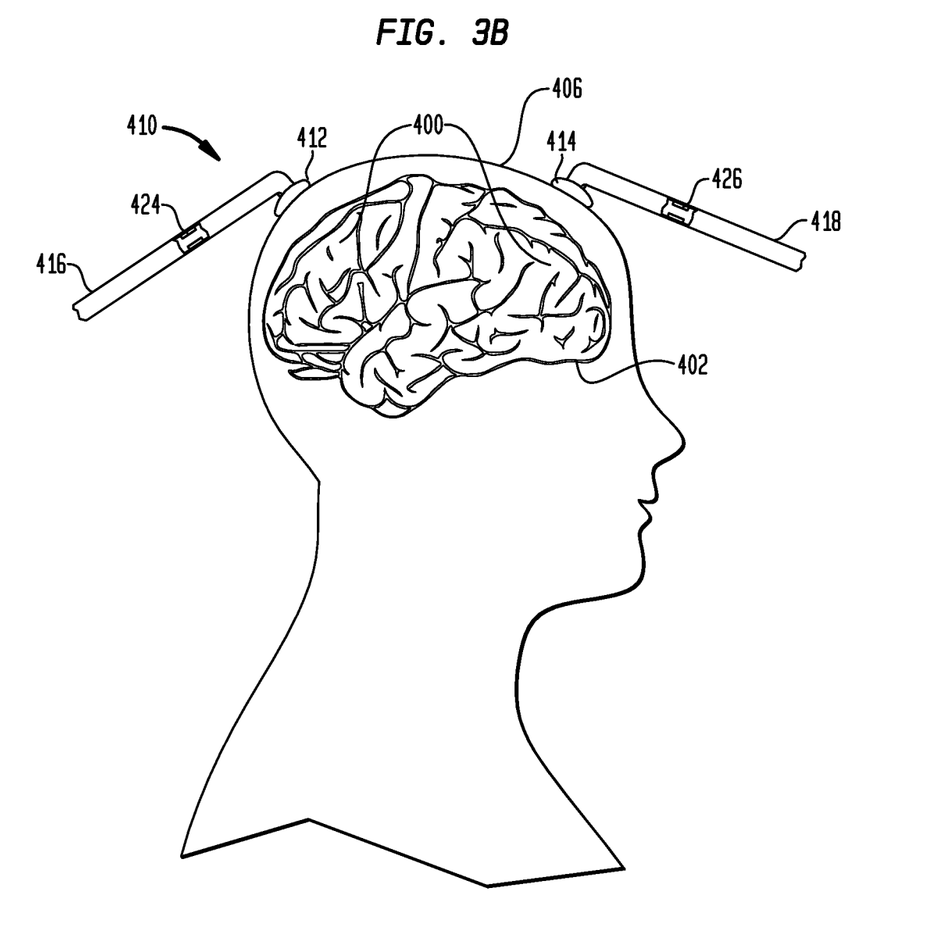

Referring now to FIGS. 3A and 3B, a general method for treating brain disorders or for improving motor and/or memory functions will now be described. One or more target regions 400 of the brain 402 are first located by the physician. The target regions 400 will of course depend on the desired treatment as described above. The target regions 400 may be identified with reference to anatomical features of the patient, such as the patient's nose or ears. In other embodiments, the target regions 400 may be identified with reference to fiducials 404 positioned in the patient's skull 406, as shown in FIG. 3A. The location of the fiducials 404 can appear on the image (or other display formats known in the art) used to present the neural activity information and identify the desired target regions 400.

Referring now to FIG. 3B, an exemplary stimulation device 410 is shown having two contact elements 412, 414 (such as a hydrogel) configured for placement on the outer surface of the patient's skull 406. Fluid tubes 416, 418 extend from contact elements 412, 414, respectively, and are coupled to an electrically conductive fluid source (not shown). In this embodiment, stimulation device 410 further includes two electrodes 424, 426 of opposite polarity positioned within the interior of fluid tubes 416, 418. In the exemplary embodiment, fluid tube 416 houses the anode and fluid tube 418 houses a cathode, although many other configurations are possible as discussed above. Internal electrical leads (not shown) couple electrodes 424, 426 to a source of electrical energy (not shown). Fluid tubes 416, 418 may also include a vacuum source (not shown) for periodically aspirating the conductive fluid.

In use, contact elements 412, 414 are positioned on the patient's skull 406 adjacent or near target regions 400 in the brain 402. In the exemplary embodiment, contact element 412 with the anode is placed adjacent a target region that is underactive (for example, the left dorsolateral prefrontal cortex or LDPFC in a patient suffering from schizophrenia) and contact element 414 with the cathode is placed adjacent a target region that is overactive (e.g., the right dorsolateral prefrontal cortex or RDPFC). An electrically conductive fluid is then delivered through fluid tubes 416, 418 to electrically couple electrodes 424, 426 to contact elements 412, 414. Contact elements 412, 414 may be attached to skull 406 in any suitable manner known to those in the art.

An electrical current is then applied to the electrodes, which flows from the electrodes 424, 426 through the conductive fluid and contact elements 412, 414 into the target regions 400 of the patient's brain 402. The current will increase the activity of nerves adjacent to the anode, while decreasing the activity of nerves adjacent to the cathode. Since the electrodes do not directly contact the tissue of the patient, the present invention reduces the potential for collateral tissue damage or necrosis and/or excessive electric fields in the tissue. In addition, the enclosures physically shield the electrode from the tissue of the patient's head, which substantially inhibits Faradic products (e.g., $H^+$, $OH^-$, $H_2O_2$) of the electrodes from contacting this tissue. Thus, the direct current can be applied to the patient's brain without the danger of such Faradic products reaching excessively high concentrations at the tissue site, allowing for a longer treatment time and/or higher current levels than is currently considered safe for the patient.

In yet another embodiment of the present invention, the electrode device may be used to amplify motor memory and/or enhance declaratory memory by delivering current oscillations in the REM bandwidth during REM sleep. In this embodiment, an oscillatory current is delivered through an electrode device as described above. The frequency of the oscillatory current will vary depending on the desired treatment. For example, to amplify motor memory, the preferred frequency range is between about 20-60 Hz. To enhance declarative memory, the preferred frequency range is between about 0-4 Hz.

In other embodiments, the invention may be used to disrupt epileptic seizures by entraining circuits at lower frequencies than supported by the epileptic neural circuit. The device may be used to desynchronize brain activity, as in the case of an epileptic patient where oversynchronization has occurred.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a disorder in a patient comprising:
    housing an electrode within an enclosure comprising an electrically conductive tissue contact element and a fluid passage;
    positioning the electrode within the fluid passage; contacting the electrically conductive tissue contact element to a skin surface of a head of the patient; delivering an electrically conductive fluid through the fluid passage to electrically couple the electrode to the contact element; and
    applying an electrical impulse through the electrode to a target region in a brain of the patient, wherein the electrical impulse is sufficient to modulate one or more neurons in the target region of the brain.

2. The method of claim 1 wherein the positioning step includes spacing the electrode at least 3 cm away from the skin surface.

3. The method of claim 1 wherein the positioning step includes spacing the electrode at least 8 cm from the skin surface.

4. The method of claim 1 wherein the electrically conductive tissue contact element comprises a gel material.

5. The method of claim 1 wherein the electrode is a first electrode, the electrically conductive tissue contact element is a first electrically conductive tissue contact element and the tissue passage is a first tissue passage, the method further comprising positioning a second electrode adjacent to and spaced from the skin surface housing the second electrode within a second enclosure comprising a second electrically conductive tissue contact element and a second fluid passage;
    positioning the second electrode within the second fluid passage;
    contacting the second electrically conductive tissue contact element to the skin surface;
    delivering an electrically conductive fluid through the second fluid passage to electrically couple the second electrode to the second contact element; and
    applying the electrical impulse from the first electrode through the target region to the second electrode.

6. The method of claim 1 wherein the electrode is an anode.

7. The method of claim 1 wherein the electrode is a cathode.

8. The method of claim 1 wherein the electrical impulse is a direct current between about 0.01 to 100 mA.

9. The method of claim 1 wherein the electrical impulse is a direct current between about 1 to 10 mA inclusive.

10. The method of claim 1 wherein the electrical impulse is sufficient to alter a firing rate of the one or more neurons in the target region.

11. The method of claim 1 wherein the electrically conductive fluid is saline.

12. The method of claim 1 wherein the electrically conductive fluid is a buffered conductive solution.

13. The method of claim 1 wherein the disorder is selected from the group consisting essentially of depression, epilepsy, fibromyalgia, schizophrenia, stroke and acute pain.

14. The method of claim 1 wherein the target region is selected from the group consisting essentially of the motor cortex, visual cortex, and prefrontal cortex of the brain.

15. A system for treating a patient's brain comprising:
a source of energy;
an enclosure having a contact element and a fluid passage, the contact element being sized and shaped for contacting an outer skin surface on a patient's head;
an electrode housed within the fluid passage of the enclosure and electrically coupled to the source of energy and the contact element of the enclosure; and
wherein the source of energy is configured to apply an electrical impulse through the electrode and the contact element of the enclosure to a target region in the patient's brain sufficient to modulate one or more neurons in the target region.

16. The system of claim 15 further comprising a source of electrically conductive fluid positioned within the fluid passage for electrically coupling the electrode to the contact element.

17. The system of claim 16 wherein the contact element comprises a gel material.

18. The system of claim 15 wherein the enclosure is a first enclosure, the electrode is a first electrode, the contact element is a first contact element and the fluid passage is a first fluid passage, the method further comprising:
a second enclosure having a second contact element and a second fluid passage, the second contact element being sized and shaped for contacting the outer skin surface of the patient's head; and
a second electrode housed within the second fluid passage of the second enclosure and electrically coupled to the source of energy, wherein the source of electrical energy is configured to apply the electrical impulse from the first electrode through the target region to the second electrode.

19. The system of claim 15 wherein the electrical impulse is a direct current between about 0.01 to 100 mA.

20. The system of claim 15 wherein the electrical impulse is a direct current between about 1 to 10 mA inclusive.

* * * * *